United States Patent [19]

Tai et al.

[11] Patent Number: 5,474,905
[45] Date of Patent: Dec. 12, 1995

[54] ANTIBODIES SPECIFIC FOR STREPTOCOCCUS PNEUMONIAE HEMIN/HEMOGLOBIN-BINDING ANTIGENS

[75] Inventors: Stanley S. Tai, Rockville, Md.; Ruth E. Winter, Belmont, Calif.

[73] Assignee: Research Corporation Technologies, Tuscon, Ariz.

[21] Appl. No.: 157,861

[22] Filed: Nov. 24, 1993

[51] Int. Cl.$^6$ ............... A61K 35/74; G01N 33/53; G01N 33/569; G01N 33/577
[52] U.S. Cl. ............ 435/7.34; 435/885; 435/975; 436/548; 530/388.4; 530/389.5
[58] Field of Search ............... 435/7.34, 7.32, 435/475, 29; 530/387.1, 388.4, 389.5, 825

[56] References Cited

U.S. PATENT DOCUMENTS

| | | | |
|---|---|---|---|
| 5,314,822 | 5/1994 | Bailey et al. | 436/252.1 |
| 5,322,788 | 6/1994 | Drouin | 435/7.34 |

FOREIGN PATENT DOCUMENTS

| | | |
|---|---|---|
| 109012 | 5/1984 | European Pat. Off. |

OTHER PUBLICATIONS

Berry et al. (1989), "Contribution of Autolysin to Virulence of *Streptococcus pneumoniae*", *Infect. Immun.*, 57:2324–2330.
Bramanti et al. (1992), "Effect of porphyrins and host iron transport proteins on outer membrane protein expression in *Porphyromonas (Bacteroids) gingivalis*: identification of a novel 26 kDa hemin–repressible surface protein", Microbial Path., 13:61–73.
Coulton et al. (1983), "Transport of Hemin by *Haemophilus influenzae* Type b", *Curr. Microbiol.*, 9:93–98.
Daskaleros et al. (1991), "Iron Uptake in *Plesiomonas shigelloids*: Cloning of the Genes for the Heme–Iron Uptake System", *Infect. Immun.*, 59:2706–2711.
Hanson et al. (1992), "Identification of genetic locus of *Haemophilus influenzae* type b necessary for the binding and utilization of heme bound to human hemopexin", *Proc. Natl. Acad. Sci.*, 89:1973–1977.
Hanson et al. (1991). "Moleculular cloning, partial purification, and characterization of a haemin–binding lipoprotein from *Haemophilus influenzae* type b", *Mol. Microbiol.*, 5:267–278.
Hanson et al. (1992), "The hbpA Gene of *Haemophilus influenzae* Type B Encodes a Heme–Binding Lipoprotein Conserved among Heme–Dependent *Haemophilus* Species", *Infect. Immun.*, 60:2257–2266.

Lee (1992), "Isolation of an Outer Membrane Hemin–Binding Protein of *Haemophilus influenzae* Type b", *Infect. Immun.*, 60:810–816.
McDaniel et al. (1986), "Analysis of surface protein of *Streptococcus pneumoniae* recognised by protective monoclonal antibodies", *Microbial Pathogenesis*, 1:519–531.
McDaniel et al. (1988), "A Pneumonococcal Surface Protein (PspB) That Exhibits the Same Protease Sensitivity as Streptococcal R Antigen", *Infect. Immun.*, 56:3001–3003.
McDaniel et al. (1991). "PspA. a Surface Protein of *Streptococcus pneumoniae*, Is Capable of Eliciting Protein against Pneumococci of More Than One Capsular Type", *Infect. Immun.*, 59:222–228.
Otto et al. (1990), "Iron–Regulated Outer Membrane Protein of Bacteroides fragilis Involved in Heme Uptake", *Infect. Immun.*, 58:3954–3958.
Paton et al. (1986), "Cloning and Expression in *escherichia coli* of the Streptococcus pneumoniae Gene Encoding Pneumolysin", *Infect. Immun.*, 54:50–55.
Stahl et al. (1972), "Pneumococcal Neuraminidase: Purification and Properties", *Biochim. Biophys. Acta*, 268:480–487.
Stojilijkovic et al., (1992), "Hemin uptake system of *Yersinia enterocolitica*: similarities with other TonB–dependent systems in Gram–negative bacteria", *EMBO*, 11:4359–4367.
Zimmermann et al. (1989), "Mechanistically Novel Iron(III) Transport System in *Serratia marcescens*", *Bacteriol.*, 171:238–243.
B. C. Lee, "Isolation of Haemin–Binding Proteins of *Neisseria Gonorrhoeae*", *J. Med. Microbiol.*, 36(2): 121–127 (1992).
Lee et al. "Identification of an Outer–Membrane Haemoglobin-Binding Protein in *Neisseria meningitidis*", J. Gen. Microbiol. 138: 2647–2656 (1992).

Primary Examiner—Toni R. Scheiner
Assistant Examiner—Nancy J. Parsons
Attorney, Agent, or Firm—Scully, Scott, Murphy & Presser

[57] ABSTRACT

The present invention relates to the isolation of newly discovered hemin/hemoglobin-binding proteins of *Streptococcus pneumoniae* with approximate molecular weights of 18, 43, 55, 66 and 76 kDa, respectively, thereby providing bacterial-derived antigens and active derivatives and parts thereof, useful in the diagnostic assays, vaccines and pharmaceutical compositions relative to these bacteria. In addition, the present invention is directed to polyclonal and monoclonal antibodies directed to the hemin/hemoglobin-binding proteins of *Streptococcus pneumoniae*. The present invention further relates to methods of diagnosing and treating human pneumococcal infections including kits therefor.

7 Claims, 9 Drawing Sheets lane 1: molecular weight marker
lane 2: cell membrane
lane 3: cytoplasmic fluid
lane 4: cell wall extract 1. Rxl Bio-Hb soluble fraction
2. Rxl Bio-Hb particulate
3. MW 1. prestained MW 2. Rxl lysate treated with both Bio-Hb and SA-agarose before SDS-PAGE.

3. Rxl lysate treated with SA-agarose but not with Bio-Hb before SDS-PAGE.

4. Rxl lysate without treatment of AP-SA and Bio-Hb before SDS-PAGE.

1. MW
2. Rx1 soluble fraction
3. Rx1 particulate fraction
4. Rx1 soluble cell wall extract
5. Rx1 cytoplasmic fraction

ANTIBODIES SPECIFIC FOR STREPTOCOCCUS PNEUMONIAE HEMIN/HEMOGLOBIN-BINDING ANTIGENS

FIELD OF THE INVENTION

The present invention relates to *Streptococcus pneumoniae* hemin/hemoglobin-binding proteins and methods of detection thereof. In particular, the present invention relates to the isolation of hemin/hemoglobin-binding proteins of *Streptococcus pneumoniae*, with molecular weights of 18, 43, 55, 66 and 76 kDa, thereby providing hemin/hemoglobin-binding protein antigens and active derivatives and parts thereof, useful in the development of diagnostic assays and vaccines for diseases caused by *Streptococcus pneumoniae* (pneumococcus). The present invention is also directed to antibodies raised to the isolated hemin/hemoglobin-binding proteins of *Streptococcus pneumoniae* or derivatives thereof to therapeutically treat human pneumococcal disease; and compositions containing antigens of *Streptococcus pneumoniae* which elicit an immune response. The present invention further relates to methods of diagnosing and treating pneumococcal infections including diagnostic kits.

BACKGROUND OF THE INVENTION

*Streptococcus pneumoniae* is a common inhabitant of the human upper respiratory tract and is a major pathogen in bacterial pneumonia, otitis media, bacteremia, and meningitis. Between 5 to 70% of all healthy individuals have isolates of *Streptococcus pneumoniae*. Changes in physical condition and immunological competence as well as the presence of an upper respiratory tract infection often lead to pneumococcal infections (i.e., infections caused by *Streptococcus pneumoniae*). Pneumococcal disease is ranked among the top ten leading causes of death in the United States. The highest risk groups are children under two years of age, the elderly, and persons with underlying diseases including acquired immunodeficiency syndrome, cirrhosis of the liver, diabetes mellitus, sickle cell disease, splenic dysfunction, acute alcoholism, congestive heart failure, and chronic obstructive pulmonary diseases.

The putative virulence factors of *Streptococcus pneumoniae* are the capsule, pneumolysin, IgA protease, purpura-producing principle, and neuraminidase. The capsule is a polysaccharide layer which surrounds the bacterium and protects the organism from phagocytosis by macrophages and polymorphonuclear leukocytes and prevents the disposition of complement complexes on the cell wall. Pneumolysin is a pneumococcal protein toxin that inhibits the migration and bactericidal activities of phagocytic cells. It represses lymphokine and the antibody producing ability of lymphocytes, activates the classical complement pathway resulting in depletion of serum opsonic activity and activates the classical complement pathway resulting in depletion of serum opsonic activity. Pneumolysin also causes cell vacuolation of respiratory epithelium structure that leads to cell death. IgA protease may destroy the protection provided by IgA-1 in the mucosa of the respiratory tract. Purpura-producing principle is a cell wall component that causes purpura and dermal hemorrhage in experimental animals. Neuraminidase is a low molecular weight enzyme that cleaves the terminal sialic acid residues from surface glycoproteins and glycolipids of eukaryotic cell membranes. The roles of these virulence factors in the pathogenesis of *Streptococcus pneumoniae* have not been directly demonstrated.

The most common method of preventing pneumococcal diseases is through antibiotic treatment and vaccination. Penicillin, which has been used for decades in the treatment of pneumococcal disease, has not been shown to improve the survival rate of invasive pneumococcal disease. Due to the wide use of antibiotics and the interspecies transfer of antibiotic resistance gene, penicillin-resistant strains of *Streptococcus pneumoniae* are common in 25% of the clinical isolates of *Streptococcus pneumoniae* in the United States. These resistant strains have also caused an outbreak of pneumococcal disease in South Africa. Thus, this wide spread occurrence of resistant *Streptococcus pneumoniae* strains poses a significant threat to the public health throughout the world.

In addition, continual use of antibiotic treatment of *Streptococcus pneumoniae* with penicillin may potentiate the development of invasive pneumococcal disease. For example, *Streptococcus pneumoniae* killed by antibiotics can release cell wall components which can induce meningeal inflammation.

One of the most ideal and effective means of controlling pneumococcal disease is vaccination. The most common vaccine currently used is composed of purified capsular polysaccharides from 23 of the most prevalent strains of *Streptococcus pneumoniae*; e.g., ACIP (1989) "Pneumococcal polysaccharide vaccine" *MMWR* 30:64–76; Smart et al. (1987) "New 23-valent pneumococcal vaccine in relation to pneumococcal serotypes in systemic and systemic disease", *J. Infect.*, 14:209–215. Active immunization elicits anticapsular antibodies that opsonize invading pneumococci which are killed by phagocytic cells. This vaccine, however, has several limitations.

First, the elicited anticapsular antibody is type-specific. Currently, there are 84 known different serotypes of *Streptococcus pneumoniae* and each serotype has a unique capsular structure. Thus, immunization with purified capsular polysaccharides for 23 of the most common strains of *Streptococcus pneumoniae* only prevents the subsequent infection by those specific pneumococcal serotypes. Therefore, an individual vaccinated by the current vaccine would not be protected from a majority of the known serotypes of *Streptococcus pneumoniae* that cause a variety of diseases. Field studies have shown that the 23-valent capsular vaccine provides protection against the vaccine-type pneumococcal infection 65% of the time and only protects against all serotypes 0–60% of the time. Second, polysaccharides are not good antigens; especially those isolated from serotypes 6 and 14 of *Streptococcus pneumoniae*, which are major pathogens in pediatric otitis media and meningitis. Third, the antibody production elicited by polysaccharide is T-cell independent and cannot be enhanced by a second immunization. Forth, the immune response to the current vaccine in the elderly and children under two years of age is weak and cannot protect them against pneumococcal infection.

An alternative approach to protecting the high risk groups from pneumococcal infection would be to isolate pneumococcal proteins that can elicit a protective immune response. Such proteins might serve as a vaccine by themselves or could be used in conjunction with successful polysaccharide vaccines or as carriers of capsular polysaccharides. Pneumolysin and pneumococcal surface protein A (PspA) have both been tested for this purpose. Studies have shown that pneumolysin is present in all serotypes of *Streptococcus pneumoniae* and exhibits a high degree of conservation in immunological cross-reactivity and nucleotide sequence. Mice immunized with pneumolysin can be rendered inactive by either site-direct or chemical mutagenesis. However, using this attenuated pneumolysin as a pneumococcal vaccine is limited in that it can only be used to halt the progress of disease caused by Streptococcus pneumoniae since pneumolysin is an intercellular protein which is released after an infection with Streptococcus pneumoniae has already occurred.

Other studies have examined pneumococcal surface protein A for its ability to produce protective antibodies. When mice were injected with PspA$^+$ pneumococci and their isogenic PspA$^-$ mutants, PspA$^+$ elicited a protective response against fatal doses of encapsulated pneumococci. Using PspA as a vaccine, however, is not effective due to significant differences in PspA-1 among the serotypes of Streptococcus pneumoniae. PspA is polymorphic. There are wide variations among strains in the molecular weight of PspA (60–200 kDa), in the cross-reactivity with monoclonal antibodies, and in the hybridization pattern with a DNA probe that encodes a portion of PspA. When mice were immunized with clones of PspA, a wide range of protection against the challenge of difference serotypes of Streptococcus pneumoniae was found. Thus, the present vaccines do not provide an effective means of preventing pneumococcal diseases.

The present invention solves the problems associated with the present antibiotic and vaccine therapies for pneumococcal diseases (i.e., diseases caused by Streptococcus pneumoniae). The present invention is directed, inter alia, to isolated hemin/hemoglobin-binding proteins of Streptococcus pneumoniae having approximate molecular weights of 18, 43, 55, 66 and 76 kDa, respectively, which are immunogenic and highly conserved among all serotypes of Streptococcus pneumoniae. Unlike the capsular polysaccharides of the 23 strains of Streptococcus pneumoniae described in the prior art, the hemin/hemoglobin-binding proteins described in this invention can serve as antigens for most, if not all, pneumococcal serotypes, are not T-cell independent and are prophylactic against pneumococcal infection. A preferred embodiment of this invention is the isolated hemin/hemoglobin-binding protein of Streptococcus pneumoniae having an approximate molecular weight of 43 kDa. These proteins overcome the limitation associated with Streptococcus pneumoniae antigens known in the art. The present invention provides antibodies to these antigens and compositions containing these antigens. The present invention also provides new vaccines and diagnostic methods including kits to both diagnose and treat human pneumococcal infections.

SUMMARY OF THE INVENTION

The present invention relates to isolated Streptococcus pneumoniae antigens and specifically hemin/hemoglobin-binding proteins of Streptococcus pneumoniae with approximate molecular weights of 18, 43, 55, 66 and 76 kDa, respectively, and their antigenically active derivatives and parts thereof.

The present invention further relates to the production of antibodies to the hemin/hemoglobin-binding antigens of this invention.

A further aspect of this invention is directed to pharmaceutical compositions containing the present hemin/hemoglobin-binding antigens of Streptococcus pneumoniae which elicit an immune response.

Another aspect of this invention is directed to using as least one of the above-identified proteins as the active component in a vaccine preferably against all serotypes of Streptococcus pneumoniae.

Yet another aspect of this invention is directed to the use of the present Streptococcus pneumoniae hemin/hemoglobin-binding proteins to generate antibodies useful in diagnostic and therapeutic techniques for human Streptococcus pneumoniae infections.

Still another aspect of this invention is directed to methods of diagnosing pneumococcal disease including the use of diagnostic kits.

These and other objects of the present invention are achieved by providing the isolated Streptococcus pneumoniae antigens of this invention which have been characterized as hemin and hemoglobin binding with approximate molecular weights of 18, 43, 55, 66 and 76 kDa, respectively. These antigens have been determined to be principally associated with the outer membrane of the Streptococcus pneumoniae and provide an excellent basis for eliciting an immunogenic reaction when infected with the bacteria. These antigens are specific to most, if not all, serotypes of the bacteria.

The present invention also contemplates antibodies raised to the newly discovered antigens and methods of detecting the presence of such antigens and antibodies including kits therefor for determining infections of Streptococcus pneumoniae. As a therapeutic, vaccines and antigenic pharmaceutical compositions containing the antigen as the active agents are also contemplated including a method of treating infections caused by Streptococcus pneumoniae with such compositions.

DETAILED DESCRIPTION OF THE INVENTION

The present invention is directed to newly isolated proteins of Streptococcus pneumoniae. These proteins have been characterized in the first instance by their hemin/hemoglobin-binding capacity. The hemin/hemoglobin-proteins of Streptococcus pneumoniae have approximate molecular weights of 18, 43, 55, 66 and 76 kDA.

Prior to this invention, the iron transport of Streptococcus pneumoniae had not been investigated. The ability of proteins described in this invention to bind hemin and hemoglobin was first determined by examining the ability of Streptococcus pneumoniae to produce siderophores to transport iron molecules using a mechanism similarly described for numerous Gram-positive bacteria. These studies revealed that *Streptococcus pneumoniae* does not produce iron-chelating siderophores when grown in low-iron medium.

Figure 1:
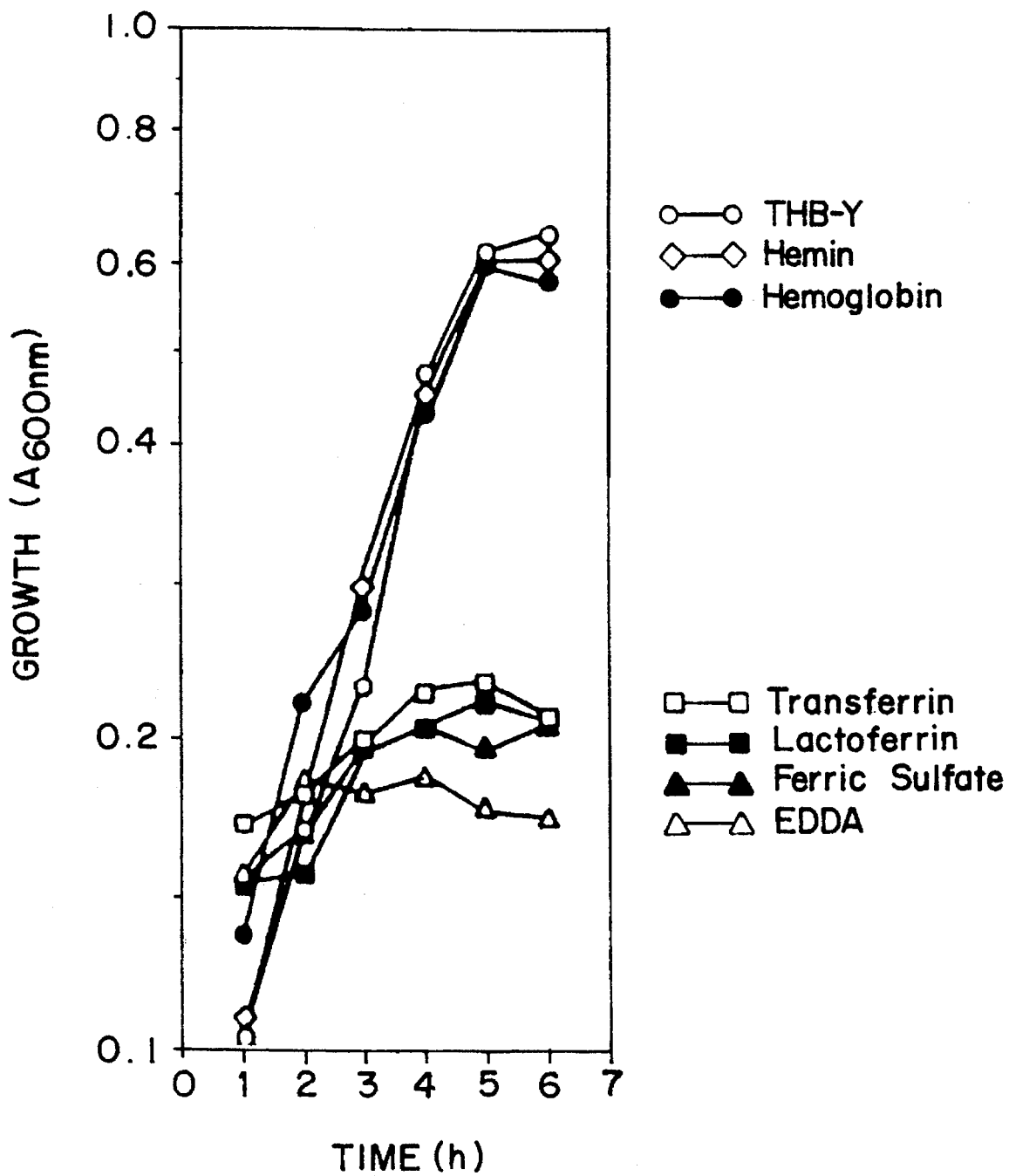
FIG. 1 shows the growth of wild-type Pn-2 cells in iron-depleted medium supplemented with different iron-containing compounds.

The next inquiry determined whether *Streptococcus pneumoniae* could directly utilize an iron source. When *Streptococcus pneumoniae* was examined for its ability to use transferrin, lactoferrin, hemoglobin, hemin or ferric sulfate under low-iron conditions, only hemin and hemoglobin was utilized as shown in FIG. 1. Hemin and hemoglobin restored the growth of *Streptococcus pneumoniae* inhibited by the presence of EDDA, while transferrin, lactoferrin or ferric iron did not. It is clear for the first time from this invention that *Streptococcus pneumoniae* has the capacity to utilize hemin.

It was further determined in accordance with the present invention that the hemin and hemoglobin utilization by *Streptococcus pneumoniae* was associated with the virulence of the bacteria.

Figure 2:
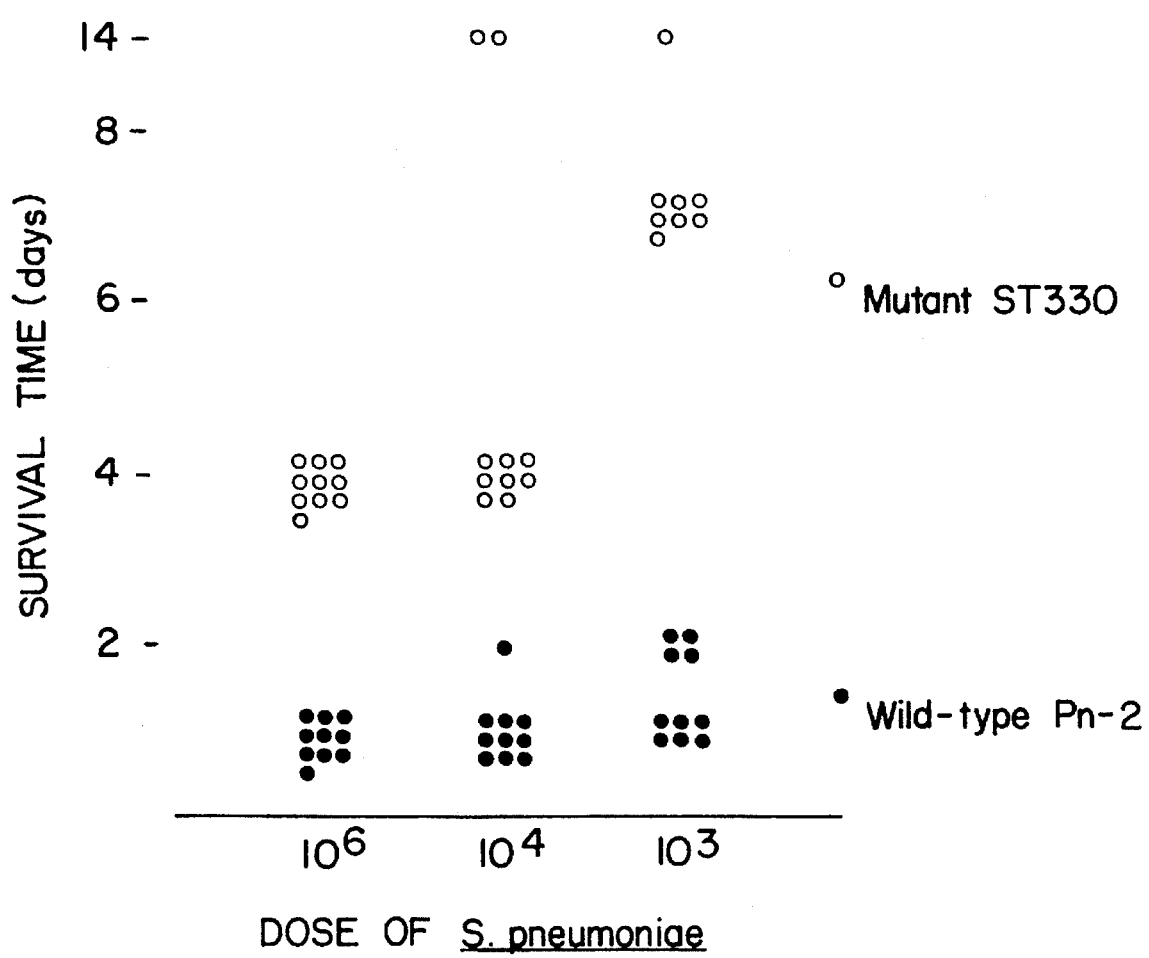
FIG. 2 shows the virulence test of mutant ST330.

The virulence of *Streptococcus pneumoniae* was evaluated on BALB/c mice. As shown in FIG. 2, the hemin-utilization mutants of *Streptococcus pneumoniae* were less virulent than the wild-type cells of *Streptococcus pneumoniae*. Thus, the present invention identifies a correlation between the hemin-utilizing capacity of *Streptococcus pneumoniae* and its bacterial virulence.

Figure 3:
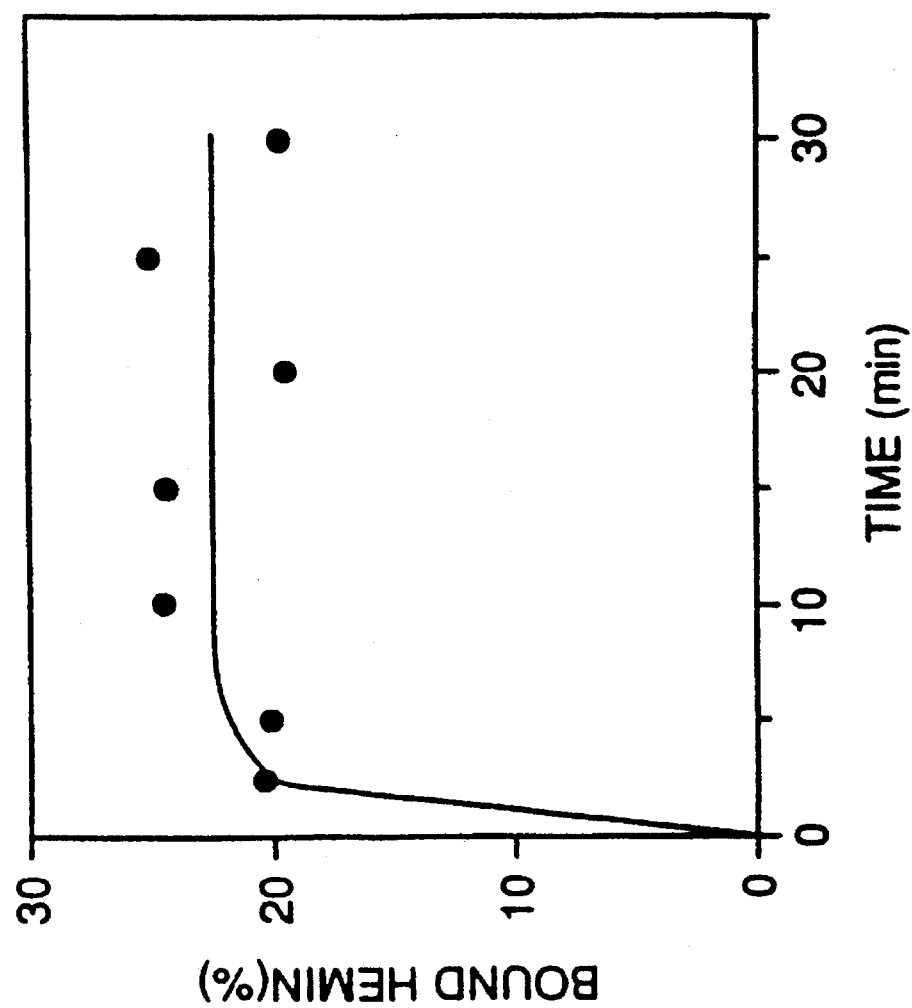
FIG. 3 shows the hemin/hemoglobin-binding activity of wild-type Pn-2 cells.

The ability of *Streptococcus pneumoniae* to bind hemin was confirmed by measuring the decrease of absorbance of 400 nm in the supernatant of a reaction mixture containing *Streptococcus pneumoniae* cells and hemin as shown in FIG. 3. This binding ability was not affected by the temperature of the reaction or by extensive washing with buffer.

Figure 4:
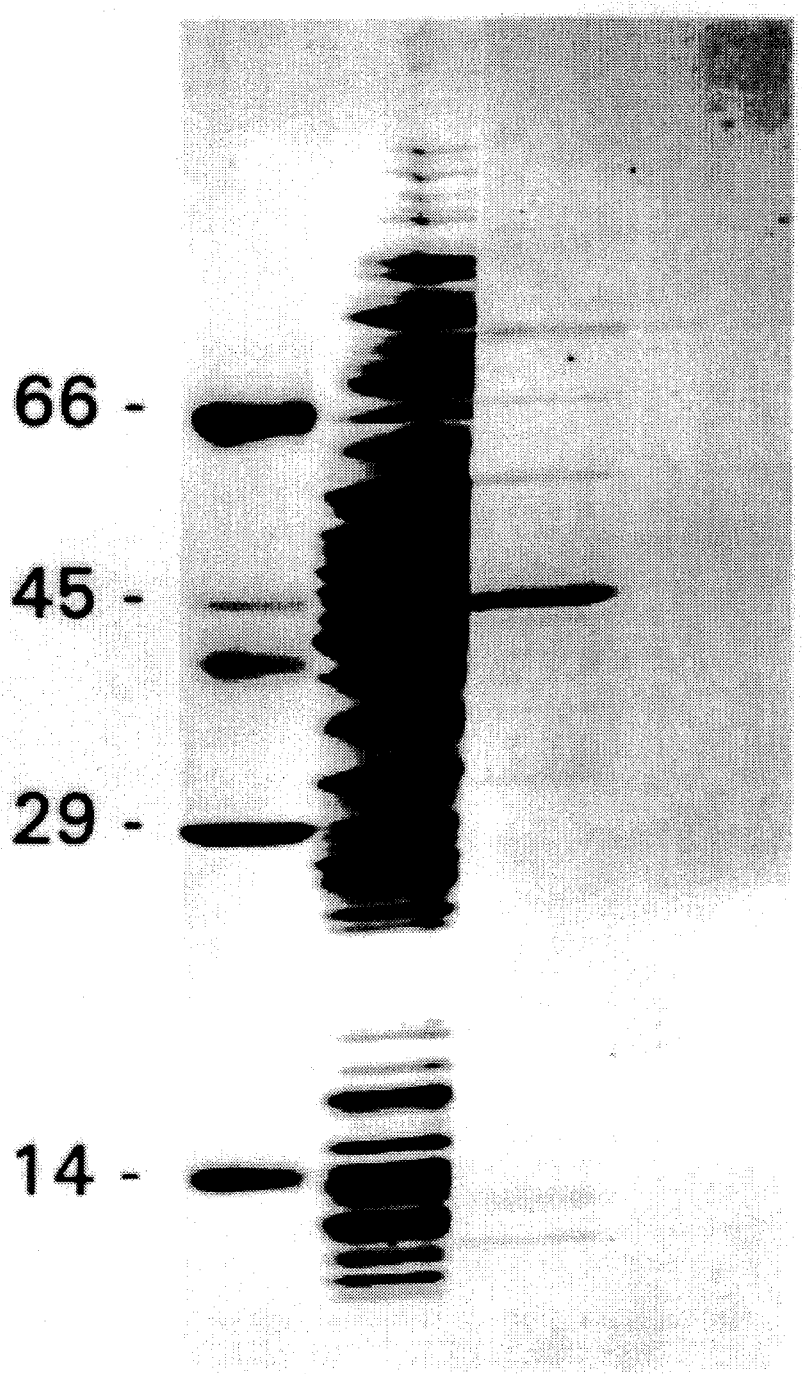
FIG. 4 shows the isolation of the hemin/hemoglobin-binding proteins of Streptococcus pneumoniae

In a first embodiment, the present invention is directed to the isolation of newly discovered hemin/hemoglobin-binding proteins, i.e., antigens of *Streptococcus pneumoniae*. In particular, the present invention describes five hemin/hemoglobin-binding protein antigens of *Streptococcus pneumoniae* with approximate molecular weights of 18, 43, 55, 66 and 76 kDa, respectively. Batch affinity chromatography was used to isolate the proteins of the present invention. The bacterial cells were lysed and the proteins were separated. These isolated proteins were identified by their migration on SDS-polyacrylamide gel electrophoresis as described in Example 4. The results are shown in FIG. 4. Four of the proteins of the present invention are associated with the outer membranes of the bacteria. These surface protein antigens include the 43, 55, 66 or 76 kDa hemin/hemoglobin-binding proteins of *Streptococcus pneumoniae*. The 18 kDa hemin/hemoglobin-binding protein was found to be a cytoplasmic protein. The preferred species of the present invention is the hemin/hemoglobin-binding protein of *Streptococcus pneumoniae* with an approximate molecular weight of 43 kDa.

The present invention further contemplates the use of the *Streptococcus pneumoniae* hemin/hemoglobin-binding proteins of the present invention to prepare antibodies. Antibodies to these *Streptococcus pneumoniae* antigens can be produced by a host of conventional means including by administering at least any one of the above-identified hemin/hemoglobin-binding protein antigens of *Streptococcus pneumoniae* to an animal to raise antibodies. Such antibodies may be monoclonal or polyclonal. Additionally, it is within the scope of this invention to include second antibodies (monoclonal or polyclonal) directed to the first antibodies discussed above.

In a further embodiment, the present invention contemplates polyclonal antibodies to the newly discovered hemin/hemoglobin-binding proteins of *Streptococcus pneumoniae*. Polyclonal antibodies are obtainable by immunization with at least one of the above-identified proteins or their active components. Active components include that region of the hemin/hemoglobin-binding necessary to elicit an immune response (i.e. produce an antibody). The methods of obtaining polyclonal antibodies are well known in the art; e.g., extensive protocols for antibody production can be found in Harlow et al., *Antibodies: A Laboratory Manual*, Cold Spring Harbor, N.Y., 1988.

A preferred embodiment of the present invention contemplates polyclonal antibodies to the hemin/hemoglobin-binding protein of *Streptococcus pneumoniae* having an appropriate molecular weight of 43 kDa. These polyclonal antibodies are prepared by injection of a suitable laboratory animal with the bacterial antigenic component, collecting serum from the animal, and isolating specific sera by any of the known immunoadsorbent techniques.

In another embodiment of the present invention, the preparation of monoclonal antibodies are contemplated for detection and diagnosis of infections caused by *Streptococcus pneumoniae*. The present invention contemplates producing monoclonal antibodies by injecting an animal with at least one of the hemin/hemoglobin-binding proteins of *Streptococcus pneumoniae* of this invention. A preferred embodiment is directed to monoclonal antibodies to the 43 kDa hemin/hemoglobin-binding protein of the present invention.

The production of monoclonal antibodies relative to the present invention is particularly preferred because of the ability to produce monoclonal antibodies in large quantities and the homogeneity of the final product. One method of producing monoclonal antibodies contemplated by this invention is the preparation of hybridoma cell lines for monoclonal antibody production derived by fusing an immortal cell line and lymphocytes sensitized against the immunogenic preparation can be accomplished by techniques which are well known to one skilled in the art. (See, e.g., Kohler, G. and Milstein, C., *Nature* 256: 495–497, 1975; *European Journal of Immunology*, 6:511–519, 1976; the teachings of which are herein incorporated by reference).

Unlike preparation of polyclonal sera, the choice of animal is dependent on the availability of appropriate immortal lines capable of fusing with lymphocytes thereof. Mouse and rat have been the animals of choice in hybridoma technology and are preferably used. Humans can also be utilized as sources for sensitized lymphocytes if appropriate immortalized human (or nonhuman) cell lines are available. For the purpose of the present invention, the animal of choice may be injected with a purified hemin/hemoglobin-binding protein of *Streptococcus pneumoniae* or an antigenic component thereof. Such antigenic component includes that portion of hemin/hemoglobin-binding protein of *Streptococcus pneumoniae* necessary to elicit an immune response. Usually the injecting material is emulsified in Freund's complete adjuvant. Boosting injections may also be required. One method of detecting antibody production contemplated by this invention is carried out by testing the antisera with an appropriately labeled antigen. Lymphocytes can be obtained by removing the spleen or lymph nodes of sensitized animals in a sterile fashion and carrying out fusion. Alternately, lymphocytes can be stimulated or immunized in vitro, as described, for example, in C.Reading, (1982) *J. Immunol. Meth.*, 53:261–291.

A number of cell lines suitable for cell fusion have been developed, and the choice of any particular cell line for hybridization protocols in the production of monoclonal antibodies is directed by any one of a number of criteria such as speed, uniformity of growth characteristics, deficiency of its metabolism for a component of the growth medium, and potential for good fusion frequency.

Methods of cell fusion induction contemplated by this invention include induction by a virus, such as Epstein-Barr on Sendai virus, or polyethylene glycol. Polyethylene glycol (PEG) is the most efficacious agent for the fusion of mammalian somatic cells. PEG itself may be toxic for cells, and various concentrations should be tested for effects on viability before attempting fusion. The molecular weight range of PEG may be varied from 1,000 to about 70% w/w in saline or serum-free medium. Exposure to PEG at 37° C. for about 30 seconds is preferred in the present case, utilizing murine cells. Extremes of temperature (i.e. about 45° C.) are avoided, and preincubation of each component of the fusion system at 37° C. prior to fusion gives optimum results. The ratio between lymphocytes and malignant cells range of from about 1:1 to about 1:10 gives good results.

The successfully fused cells can be separated from the myeloma line by any technique known by the art. The most common and preferred method is to choose a malignant line which is Hypoxanthine Guanine Phosphoribosyl Transferase (HGPRT) deficient, which will not grow in an aminopterin-containing medium used to allow only growth of hybrids and which is generally composed of hypoxanthine $1\times10^{-4}$M, aminopterin $1\times10^{5}$M, and thymidine $3\times10^{-5}$M, commonly known as the HAT medium. The fusion mixture can be grown in the HAT-containing culture medium immediately after the fusion 24 hours later. The feeding schedules usually entail maintenance in HAT medium for two weeks and then feeding with either regular culture medium or hypoxanthine, thymidine-containing medium.

The growing colonies described above are tested for the presence of monoclonal antibodies that recognize the antigenic preparation, wherein said antigenic preparation includes at least one of the above-identified hemin/hemoglobin-binding Streptococcus pneumoniae proteins of the present invention or an antigenic derivative thereof. For purposes of this invention, derivatives thereof include the active portion of the Streptococcus pneumoniae hemin/hemoglobin-binding protein which is antigenic and elicits an immune response in animals.

Hybridoma antibodies are identified by using an assay where the antigen is bound to a solid support and allowed to react to hybridoma supernatants containing putative antibodies. The presence of antibodies is shown by "sandwich" techniques using a variety of indicators, as discussed in further detail below. Most of the common methods are sufficiently sensitive for use in the range of antibody concentrations secreted during hybrid growth.

Cloning of antibody-secreting hybrids can be carried out after 21-23 days of cell growth in selected medium. Methods of cloning alternatively contemplated by this invention include performing cell limiting dilution in fluid phase or by directly selecting single cells growing in semi-solid agarose. For limiting dilution, cell suspensions are diluted serially to yield a statistical probability of having only one cell per well. For the agarose technique, hybrids are seeded in a semisolid upper layer, over a lower layer containing feeder cells. The colonies from the upper layer may be picked up and eventually transferred to wells.

Antibody-secreting hybrids can be grown in various tissue culture flasks, yielding supernatants with variable concentrations of antibodies. In order to obtain higher concentrations, hybrids may be transferred into animals to obtain inflammatory ascites. Antibody-containing ascites can be harvested 8-12 days after intraperitoneal injection. The ascites contain a higher concentration of antibodies but include both monoclonals and immunoglobulins from the inflammatory ascites. Antibody purification may then be achieved by, for example, affinity chromatography.

The present invention further contemplates the detection of antibodies of Streptococcus pneumoniae using convention methods (i.e., collecting serum or spinal fluid and employing an assay to determine the presence of antibodies of Streptococcus pneumoniae). The detected antibody level may be compared to normal Streptococcus pneumoniae antibody levels to determine the presence of pneumococcal infection.

The present invention also contemplates antibodies of Streptococcus pneumoniae or derivatives thereof to therapeutically treat human pneumococcal disease (i.e., by using said antibodies in a therapeutic composition or vaccine).

Another embodiment of the present invention relates to a pharmaceutical composition for stimulating an immune response to infectious Streptococcus pneumoniae. The composition includes at least one of the hemin/hemoglobin-binding proteins as an antigenic agent or at least an antigenicallly active portion thereof, i.e., antigenic derivative thereof, in a pharmaceutically acceptable carrier. The composition is administered, i.e., an effective amount of said active agent, under conditions sufficient to cause the production of antibodies to Streptococcus pneumoniae.

The efficacy of the composition and method requires only that an immune response to at least one of the hemin/hemoglobin-binding proteins of Streptococcus pneumoniae is elicited.

The present invention is further directed to the preparation and use of a vaccine composition for the treatment of human pneumococcal disease. The vaccine includes at least one of the isolated hemin/hemoglobin-binding proteins of this invention as an active agent in a pharmaceutically acceptable vehicle. The vaccine can also include other conventional constituents. In particular, the present invention contemplates utilizing at least one of the Streptococcus pneumoniae hemin/hemoglobin-binding protein antigens in a pharmaceutically acceptable vehicle. The preferred embodiment of the present invention contemplates producing a vaccine against human pneumococcal disease by suspending the hemin/hemoglobin-binding protein antigen with an approximate molecular weight of 43 kDa in a suitable pharmaceutically acceptable vehicle.

Previously used vaccines have generally comprised purified capsular polysaccharides from 23 of the most prevalent strains of Streptococcus pneumoniae. The present invention contemplates a conventional vaccine wherein the isolated hemin/hemoglobin-binding protein of Streptococcus pneumoniae are inactivated by formalin, acetone, heat, phenal or other treatments. Administration of a vaccine to an individual contemplated by the present invention may be by any known or standard techniques. Methods of administration of the vaccine contemplated by this invention may include intravenous injection of the antigen, that allow the carrier microbe to reach the bloodstream.

Vaccines of the present invention may be administered parenterally (e.g., by intramuscular, subcutaneous, or intravenous injection). The amount required will vary with the antigenicity of hemin/hemoglobin-binding proteins and need only be an amount sufficient to induce an immune response typical of existing vaccines. Routine experimentation will easily establish the required amount. Typical initial dosages of vaccine could be about 0.001–100 mg antigen/kg body weight, with increasing amounts or multiple dosages used as needed to provide the desired level of protection.

The pharmaceutical carrier in which the vaccine is suspended or dissolved may be any solvent or solid that is non-toxic to the inoculated animal and compatible with the carrier organism or antigenic gene product. Suitable pharmaceutical carriers include liquid carriers, such as normal saline and other non-toxic salts at or near physiological concentrations, and solid carriers, such as talc or sucrose. Adjutants, such as Freund's adjuvant, complete or incomplete, may be added to enhance the antigenicity via the bronchial tubes, the vaccine is suitably present in the form of an aerosol. Booster immunizations may be repeated numerous times with beneficial results.

In a preferred embodiment, the present invention contemplates a vaccine specific to the 43 kDa hemin/hemoglobin-binding protein antigen of *Streptococcus pneumoniae.*

The present invention further contemplates a method of diagnosing infectious diseases caused by *Streptococcus pneumoniae* comprising detecting the presence of at least one of the hemin/hemoglobin-binding protein antigens of *Streptococcus pneumoniae* in a serum or spinal fluid sample. Specifically, the present method includes contacting a serum or spinal fluid sample with an antibody to at least one of the hemin/hemoglobin-binding proteins of the present invention or their antigenic derivatives for a time and under conditions sufficient to detect the presence of said antigen and thus detect the infectious bacteria. In a further embodiment this method contemplates contacting a serum or spinal fluid sample with any assay which detects the presence of any of at least one of the antigens or their antigenic derivatives of the present invention.

*Streptococcus pneumoniae* is part of the normal flora in the respiratory tract of healthy individuals, however, only individuals who are infected with *Streptococcus pneumoniae* have the bacteria present in their bloodstream or spinal fluid. Pneumoniae infections are currently diagnosed by collecting serum or spinal fluid from the individual and determining whether *Streptococcus pneumoniae* is present in the collected samples using conventional bacterial culture techniques. The growth culture is incubated for a minimum of two days and is not highly accurate. The present invention solves the problems of delayed diagnosis and inaccuracy associated with the current diagnostic tests by employing quick and accurate immunoassay techniques directed to the *Streptococcus pneumoniae* in serum and spinal fluid samples.

Several diagnostic methods are contemplated for the present invention. The present invention contemplates the use of the above-described antigens in a detection assay (immunoassay) for diseases caused by *Streptococcus pneumoniae.*

A wide range of immunoassay techniques are available as can be seen by reference to Harlow et al., supra. This, of course, includes both single-site and two-site, or "sandwich", assays of the non-competitive types, as well as in traditional competitive binding assays. Sandwich assays are among the most useful and commonly used assays and are favored for use in the present invention. A number of variations of the sandwich assay techniques exist, and all are intended to be encompassed by the present invention.

In a typical forward assay, an unlabeled antibody is immobilized in a solid substrate and the sample to be tested is brought into contact with the bound molecule. After a suitable period of incubation (i.e., a period of time sufficient to allow formation of an antibody-antigen binary complex) a second antibody, labeled with a reporter molecule capable of producing a detectable signal, is added and the mixture is incubated for a time sufficient to allow the formation of a ternary complex of antibody-labeled antibody. Any unreacted material is washed away, and the presence of the antigen is determined by observation of the visible signal produced by the reporter molecule. The results may either be qualitative, by simple observation of the visible signal, or may be quantitated by comparing with a control sample containing known amounts of hapten.

Variations on the forward assay are contemplated by this invention. One such variation includes a simultaneous assay, in which both sample and labeled antibody are added simultaneously to the bound antibody. A second variation contemplated by this invention includes a reverse assay in which the labeled antibody and sample to be tested are first combined, incubated and then added to the unlabeled surface bound antibody. These techniques are well known to those skilled in the art, and the possibility of minor variations will be readily apparent to those skilled in the art.

As used herein, "sandwich assay" is intended to encompass all variations on the basic two-site technique. For example, these antibodies may be used to detect *Streptococcus pneumoniae* by use of specific antigenic determinants thereof (i.e., the 18, 43, 55, 66 and 76 kDa hemin/hemoglobin-binding proteins of *Streptococcus pneumoniae*) as immobilized immunoadsorbents. Serum is obtained from subjects to be tested and the serum contacted to the immobilized viral immunoadsorbents. If the serum contains antibodies to said immunoadsorbents, an antibody-adsorbent conjugate will result. After excess serum and non-bound antibodies are removed, a second antibody specific to a first antibody, said first antibody being capable of forming a conjugate with said immunoadsorbent, is added. This results in a double antibody-adsorbent conjugate. This double antibody-adsorbent conjugate will only result if the test serum contains antibodies to the immunoadsorbent. Consequently, standard detection techniques can be used to identify the conjugate.

An alternative immunoassay contemplated by the present invention is the competitive binding assay. In this assay, an antibody specific for the molecule of interest (i.e., the hemin/hemoglobin-binding protein antigens) is combined with specific volumes of solutions containing an unknown amount of the molecule to be detected and a solution containing a detectably labeled known amount of the molecule to be detected or an analog thereof. Labeled and unlabeled molecules then compete for the available binding sites on the antibody. Phase separation of the free and antibody-bound molecules allows measurement of the amount of label present in each phase, thus indicating the amount of antigen or hapten in the sample being tested. A number of variations in this general competitive binding assay currently exist. All conventional assay materials may be used in the present invention.

In any of the known immunoassays, for practical purposes, one of the antibodies to the antigen will be typically bound to a solid phase and a second molecule. This second molecule may be either the second antibody in a sandwich assay, or, in a competitive assay, the known amount of antigen with a detectable label or reporter molecule to allow visual detection of an antibody-antigen reaction. When two antibodies are employed, as in the sandwich assay, it is only necessary that one of the antibodies be specific for, e.g., the hemin/hemoglobin-binding proteins of *Streptococcus pneumoniae.* The following description will relate to a discussion of a typical forward sandwich assay; however, the general techniques are to be understood as being applicable to any of the contemplated immunoassays and are contemplated by the present invention. The preferred embodiment of this invention contemplates the use of the hemin/hemoglobin-binding protein derived antigen of *Streptococcus pneumoniae* with an approximate molecular weight of 43 kDa in any one of the immunoassays described in this invention.

A further assay which can be used in a method of diagnosing disease caused by *Streptococcus pneumoniae* contemplated by the present invention is a forward sandwich assay.

In the typical forward sandwich assay, a first antibody having specificity for, e.g., the *Streptococcus pneumoniae* hemin/hemoglobin-binding proteins or its antigenic fragments is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well-known in the art and generally consist of cross-linking, covalently binding, or physically adsorbing the molecule to the insoluble carrier. Following binding, the polymer-antibody complex is washed in preparation for the test sample. An aliquot of the sample to be tested is then added to the solid phase complex and incubated at 25° C. for a period of time sufficient to allow binding of any subunit present in the antibody. The incubation period will vary, but will generally be in the range of about 2–40 minutes. Following the incubation period, the antibody subunit solid phase is washed and dried and incubated with a second antibody specific for a portion of the hapten. The second antibody is linked to a reporter molecule which is used to indicate the binding of the second antibody to the hapten.

By "reporter molecule", as used in the present specification and claims, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionucleotide-containing molecules.

An alternative assay contemplated by the present invention for diagnosing *Streptococcus pneumoniae* infections is an enzyme immunoassay. In an enzyme immunoassay (EIA), an enzyme is conjugated to the second antibody, generally by means of glutaraldehyde or periodate. As will be readily recognized, however, a wide variety of different conjugation techniques exist, which are readily available to the skilled artisan and applicable to the present invention. Commonly used enzymes include horseradish peroxidase, glucose oxidase, beta-galactosidase and alkaline phosphates, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; and for peroxidase conjugates, 1,2-phenylenediamine, 5-aminosalicyclic acid, or tolidine are commonly used. It is also possible to employ fluorogenic substrates, which yield a fluorescent product rather than the chromogenic substrates noted above.

In all cases, the enzyme-labeled antibody is added to the first antibody hapten complex, allowed to bind, and then excess reagent is washed away. A solution containing the appropriate substrate is then added to the ternary complex of antibody-antigen-antibody. The substrate will react with the enzyme linked to the second antibody, giving a qualitative visual signal, which may be further quantitated, usually spectrophotometrically, to give an indication of the amount of hapten which was present in the sample.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic color visually detectable with a light microscope. As in the EIA, the fluorescent labeled antibody is allowed to bind to the first antibody-hapten complex. After washing off the unbound reagent, the remaining ternary complex is then exposed to the light of the appropriate wavelength. The fluorescence observed indicates the presence of the hapten of interest. Immunofluorescence and EIA techniques are both very well established in the art and are particularly preferred for the present method. However, other reporter molecules, such as radio-isotope, chemiluminescent of bioluminescent molecules, may also be employed. It will be readily apparent to the skilled technician how to vary the procedure to suit the required purpose.

In a preferred embodiment, the present invention uses the *Streptococcus pneumoniae* hemin/hemoglobin-binding protein in enzyme immunoassays for selective detection of human infections caused by *Streptococcus pneumoniae* such as lobar pneumonia, bacteremia, otitis media and meningitis. EIA can give a clear, rapid result in about 2 hours and can therefore be more convenient and efficient and less expensive than a DNA probe test.

A preferred embodiment of the present invention further uses an ELISA (enzyme-linked immunoabsorbent assay) test for the presence of antibodies to *Streptococcus pneumoniae* in serum from patients with pneumococcal disease. The 43 kDa hemin/hemoglobin-binding protein of *Streptococcus pneumoniae* is preferred, for example, to coat microtiter plates.

The present invention also provides a method of treating pneumococcal infections which method includes the administration of at least one of the antigens of the present invention or their antigenic derivatives in an amount and for a time sufficient to elicit an immune response, i.e., to raise antibodies to the antigen and thus the bacteria.

In a further embodiment, the present invention provides a kit for the detection of *Streptococcus pneumoniae* hemin/hemoglobin-binding protein. The kit contemplated by this invention is compartmentalized to receive at least a first container adapted to contain an antibody having detectable specificity for the *Streptococcus pneumoniae* hemin/hemoglobin-binding protein; and alternatively a second container containing an antibody specific for first antibody and labeled with, for example, a reporter molecule capable of providing a detectable positive signal. If the reporter molecule is an enzyme, then a third container, containing a substrate for said enzyme is provided.

Other embodiments of the kit include at least one container adapted to contain reagents necessary to determine the presence of at least one of the antigens of the present invention or their antigenic derivatives.

These and other aspects of the present invention are illustrated and supported by the following nonlimiting examples.

EXAMPLE 1

Strains and growth conditions. The *Streptococcus pneumoniae* strains used were virulent serotype 2 (Pn-2) and non-encapsulated Rx-1. These organisms were routinely grown in either Todd-Hewitt Broth (THB) or THB supplemented with 0.5% yeast extract (THB-Y) at 37° C. in an atmosphere of 5% $CO_2$. Iron-restricted growth was achieved by growing cells in the deferrated medium prepared either by the treatment of medium with 2% chelex-100 (BioRad, Hercules, Calif.) for 4 h before autoclaving or by the addition of ethylenediamine di-o-hydroxyphenylacetic acid (EDDA, Sigma, St. Louis, Mo.) to a final concentration of 700 μM. Chelex 100-treated medium was supplemented with 100 μM calcium chloride and 1 mM magnesium sulfate before use. The growth of Pn-2 in chelex 100-treated medium was slow but was totally inhibited in the EDDA-containing medium. THB or THB-Y supplemented with 100 μM ferric sulfate was used as a high-iron medium. *E. coli* strain DH5α and *C. diphtheria* strain C7 were used as positive controls for siderophore production and were maintained in Luria broth and PGT-maltose medium respectively. All *E. coli* and *C. diphtheria* cultures were incubated at 37° C. with shaking.

EXAMPLE 2

Assays for siderophore production. Studies from *E. coli* and other Gram-negative enteric bacteria indicate that siderophore synthesis is negatively regulated by iron. To assess siderophore production by *Streptococcus pneumonia*, the culture supernatant of Pn-2 grown in low-iron medium deferrated by chelex 100 was used. A bioassay examining the siderophore production and utilization was performed as follows. A THB-Y agar plate containing EDDA was seeded with approximately $10^5$ colony forming units (CFU) of Pn-2 cells. Various amounts of culture supernatant of Pn-2 grown in the chelex 100-treated THB-Y medium were spotted into the pre-cut wells on the plates. The growth of Pn-2 cells was examined after incubation at 37° C. for 48 h. If siderophores were present in the culture supernatant, they would scavenge iron molecules from EDDA and stimulate the growth of Pn-2 cells demonstrated by a zone of growth surrounding the well. The Arnow and Czaky reactions were used as chemical methods to test the presence of phenolate- and hydroxamate-type siderophores respectively; as described by Arnow, L. E. (1937) "Colorimetric determination of the components of 3,4-dihydroxyphenylalanine-tyrosine mixture", *J. Biol. Chem.*, 228:531–537, and Czaky, T. Z. (1948) on the estimation of bound hydroxylamine in biological materials, *Acta Chem. Scand*, 2:450–454. The culture supernatant of *E. coli* DH5α grown in chelex 100-treated THB-Y was used as a positive control for phenolate. The ability to produce iron-chelating compounds by *S. pneumoniae* was also examined by the universal siderophore detection assay; as described by Schwyn and Neilands (1987), "Universal chemical assay for the detection and determination of siderophores" *Anal Biochem.* 160:47–56. However, the growth requirement of *Streptococcus pneumoniae* is complex and ingredients in THB-Y medium interfere with the chrome azurol S reaction. To circumvent this difficulty, Pn-2 cells were cultured in the deferrated modified PGT medium which has been successfully used for the detection of siderophore produced by *C. diphtheria*, as described by Tai et al. (1990) "Coordinate regulation of siderophore and diphtheria tox production by iron in corynebacterium diphteriae" *Microb. Pathog.* 9:267–273. An aliquot (10 μl) of log-phase Pn-2 cells was transferred to 10 ml of modified PGT medium deferrated by chelex 100-treatment and incubated at 37° C. until late-log phase of growth. The culture supernatant of Pn-2 cells was collected after centrifugation at 10,000×g for 10 min and tested for siderophore production. *C. diphtheria* was used as a positive control in the chrome azurol S reaction.

EXAMPLE 3

Hemin/Hemoglobin-Binding Assay.

The hemin/hemoglobin-binding activity of Pn-2 cells was measured as described previously by Carman et al. (1990) "Hemin levels in culture medium of Porphyromonas (Bacteroides) gingivalis regulate both hemin/hemoglobin-binding and trypsinlike protase production." *Infect. Immun,* 58:4016–4019. An 100 ml culture of late-log Pn-2 cells ($A_{600\ nm}$ =0.8) was harvested, washed twice with phosphate buffer is saline, and suspended in PBS to an absorbance at 600 nm of 2. The reaction mixture for binding assay, containing hemin (16 μg/ml) and various amounts of Pn-2 cells, was incubated at 37° C. for 30 min and centrifuged at 10,000×g for 5 min. The absorbance of supernatant at 400 nm was measured. The decrease of $A_{400\ nm}$ in supernatant represented the binding of hemin by Pn-2 cells.

EXAMPLE 4

Identification of Hemin/Hemoglobin-Binding Protein.

A batch affinity chromatography method described by Schryuers, A. B. (1989) "Identification of transferrin and lacoferrin-binding proteins in Haemophilus influenzae", *J. Med. Microbiol.*, 29:121–130 for the isolation of a transferrin binding protein from *H. influenzae* was used to identify the hemin/hemoglobin-binding proteins of *Streptococcus pneumoniae*. An 100 ml culture of Rx-1 in the late-log phase of growth was harvested, washed twice with 50 mM Tris-100 mM NaCl buffer pH 8.0), and suspended in 1 ml of the same buffer. Cells were disrupted in a mini-bead beater (Biospec Products, Bartlesville, Okla.) for 5 min. After the large cell debris and unbroken cells were cleaned by centrifuged at 3,000 for 5 min, the supernatant was mixed with 100 μl of a 2-fold diluted hemin-agarose suspension (Sigma) and incubated with gentle agitation at 37° C. for 60 min. The agarose beads were pelleted by centrifugation at 750×g for 3 min and suspended in 1 ml of 50 mM Tris-100 mM NaCl buffer (pH 8.0). Ethylenediamine tetraacetic acid (EDTA, Sigma) and sarcosyl were added to the reaction mixture to a final concentration of 10 mM and 0.75% respectively. After incubation at room temperature for 60 min, the mixture was centrifuged at 750×g for 3 min to remove the unbound proteins. The agarose beads were then washed three times with 50 mM Tris-1M NaCl buffer (pH 8.0) containing 10 mM EDTA and 0.5 sarcosyl, twice with the same buffer without EDTA and sarcosyl, and then once with 50 mM Tris-100 mM NaCl buffer (pH 8.0). After the final wash, the pellet was suspended into 40 μl of two-fold concentrated sample buffer for SDS-polyacrylamide gel electrophoresis, heated at 100° C. for 5 min, quickly cooled on ice for 1 min, and centrifuged at 750 g for 3 min. The supernatant was immediately transferred to a separate tube and analyzed by 10% SDS-PAGE.

EXAMPLE 5

Isolation of iron-uptake mutants. Chemical mutagenesis using N-methyl-N'-nitro-N-nitrosoquanidine (NTG, Sigma) to isolate iron-uptake mutants of *S. pneumoniae* was performed as described by Cryz et al. (1983) "Regulation of toxinogenesis in corynebacterium diphtheria:mutations in the bacterial genome that alter the effects of iron on toxin production" (1993). *J. Bacteriol.*, 154, 245–252. Briefly, 100 ml of log-phase Pn-2 cells ($A_{600}$=0.5) grown in THB-Y medium were harvested by centrifugation at 12,000 g for 15 min at 4° C., washed twice with 10 ml of 50 mM Tris-50 mM maleate buffer (pH 6.0), and suspended in 0.5 ml of buffer. NTG was added to the cell suspension to a final concentration of 670 µg/ml. After incubation at 37° C. for 15 min without shaking, cells were washed twice with 10 ml of Tris-maleate buffer and suspended in 10 ml of THB-Y medium. Less than 1% of the Pn-2 cells survived after NTG treatment. To screen iron uptake mutants, streptonigrin, an antibiotic that is toxic to cells having active iron uptake activity, was used as previously described by Yeowell and White (1982) "Iron requirement in the bactericidal mechanism of streptonigrin." *Antimicrols. Agents Chemother.*, 22:961–968. This method has been used in the isolation of iron uptake mutants of *E. coli* as described by Zimmermann et al. (1984) Exogenous induction of the iron dicitrate transport system of *Escherichia coli. J. Bacteriol*, 189:271–277, *Serratia marcescens*, as described by Zimmermann et al., (1989) "Mechanistically novel iron (14) transport system in serratia marcesceus". *J. Bacteriol.*, 171:238–243, and *Neisseria meningititis* Dyer et al. (1987) "Isolation by streptonigrin enrichment and characterization of a transferrin-specific iron uptake mutant of Neisseria meningitides", *Microb. Pathog*, 3:351–363. An aliquot (0.5 ml) of mutagenized Pn-2 cells was transferred to 5 ml THB-Y medium and incubated at 37° C. for 4 h. Streptonigrin was added to the culture to the minimal inhibitory concentration for wild-type Pn-2 cells, 5 µg/ml, determined in the preliminary studies. After incubation for another 5 h, cells were mixed with top agar containing 5 µm/ml streptonigrin, poured onto the THB-Y plates, and incubated at 37° C. overnight. Streptonigrin-resistant colonies were collected and tested for hemin utilization in the THB-Y medium containing EDDA.

Virulence studies. The virulence of *S. pneumoniae* was evaluated on BALB/c mice. Cells of wild-type Pn-2 and hemin-utilizing mutant ST330 were grown to mid-log phase, harvested, washed twice and suspended in PBS to the volume of the original cell culture. Aliquots (100 µl) of serial dilutions of cells were intraperitoneally injected into mice. A group of 10 mice was used for every dilution. The survival time of mice was recorded and data was analyzed by the Fisher Exact test. The results are shown in FIG. 2.

EXAMPLE 6

Figure 5:
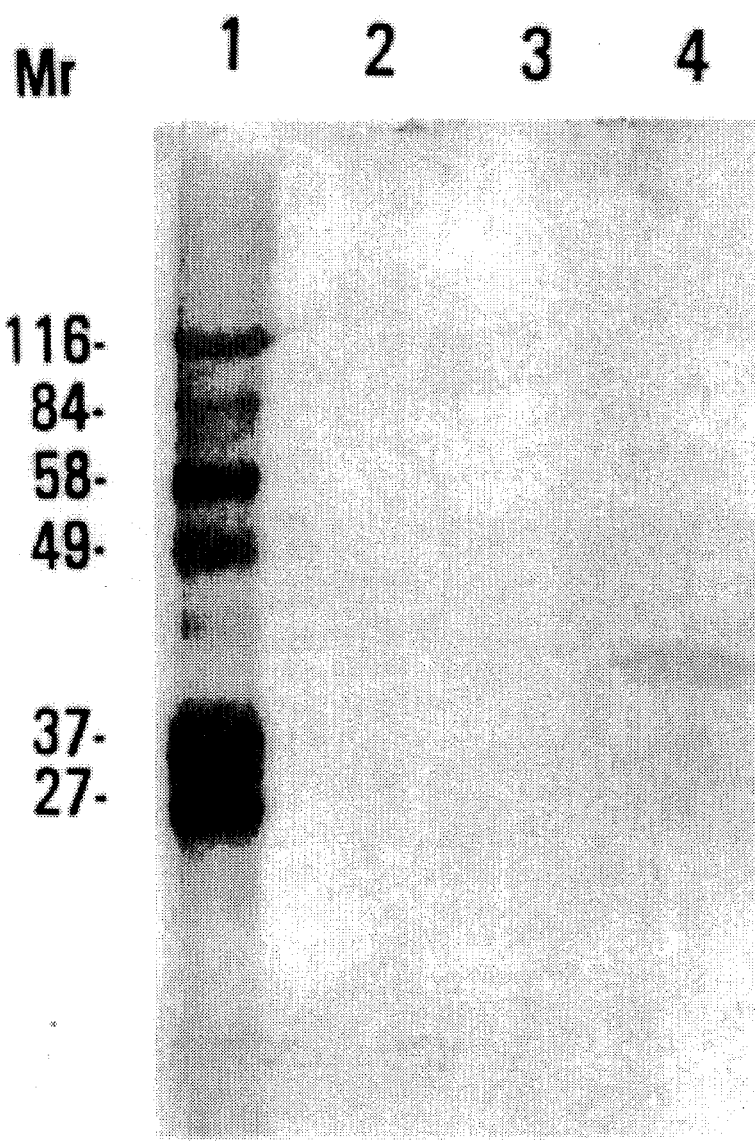
FIG. 5 shows the localization of the 43 kDa hemin/hemoglobin-binding protein.

Localization of the 43-kDa hemin/hemoglobin-binding protein. Polyclonal antibodies against the purified 43-kDa hemin/hemoglobin-binding protein was prepared in rabbits and were used to determine the location of hemin/hemoglobin-binding protein in *Streptococcus pneumoniae*. The cellular fractions of *Streptococcus pneumoniae* were prepared according to the method described previously by McDaniel et al. (1987) "Use of insertion inactivation to facilitate studies of biological properties of pneumococcal surface protein A (PspA)", *J. Exp. Med.*, 165:381–394. Pneumoniae damages human respiratory epithelium in vitro", Chest 95 Suppl.. 221S with modifications. A 100 ml of the late-log phase culture of Pn-2 cells were harvested by centrifugation at 4,000 g, washed with phosphate buffer and saline (PBS), and resuspended in 3 ml of PBS containing 20% sucrose and 50 mM $MgCl_2$. After 23 h at room temperature, the suspension was centrifuged (4,000×g for 10 min) to pellet protoplasts. The supernatant was further centrifuged at 10,000×g for 20 min to remove the insoluble portion of cell wall. After the second centrifugation, the supernatant was used as cell wall extract. Protoplasts were washed with PBS-sucrose buffer and lysed by the addition of five volumes of cold sterile water. The suspension was centrifuged at 4,000×g to remove any particulate materials. The supernatant was further centrifuged at 102,000×g for 1 h. The pellet was comprised of the cell membrane and the supernatant was comprised of the cytoplasmic fluid. Proteins in the cell wall extract and in the cytoplasmic and cell membrane fractions were separated by SDS-PAGE, transferred to nitrocellulose paper, and analyzed by Western blotting using an alkaline phosphatase based detection system. Results are shown in FIG. 5. Anti-hemin/hemoglobin-binding protein antibodies reacted with a 43-kDa protein in the cell wall extract, not in cytoplasmic fluid and membrane fractions.

EXAMPLE 7

Figure 6:
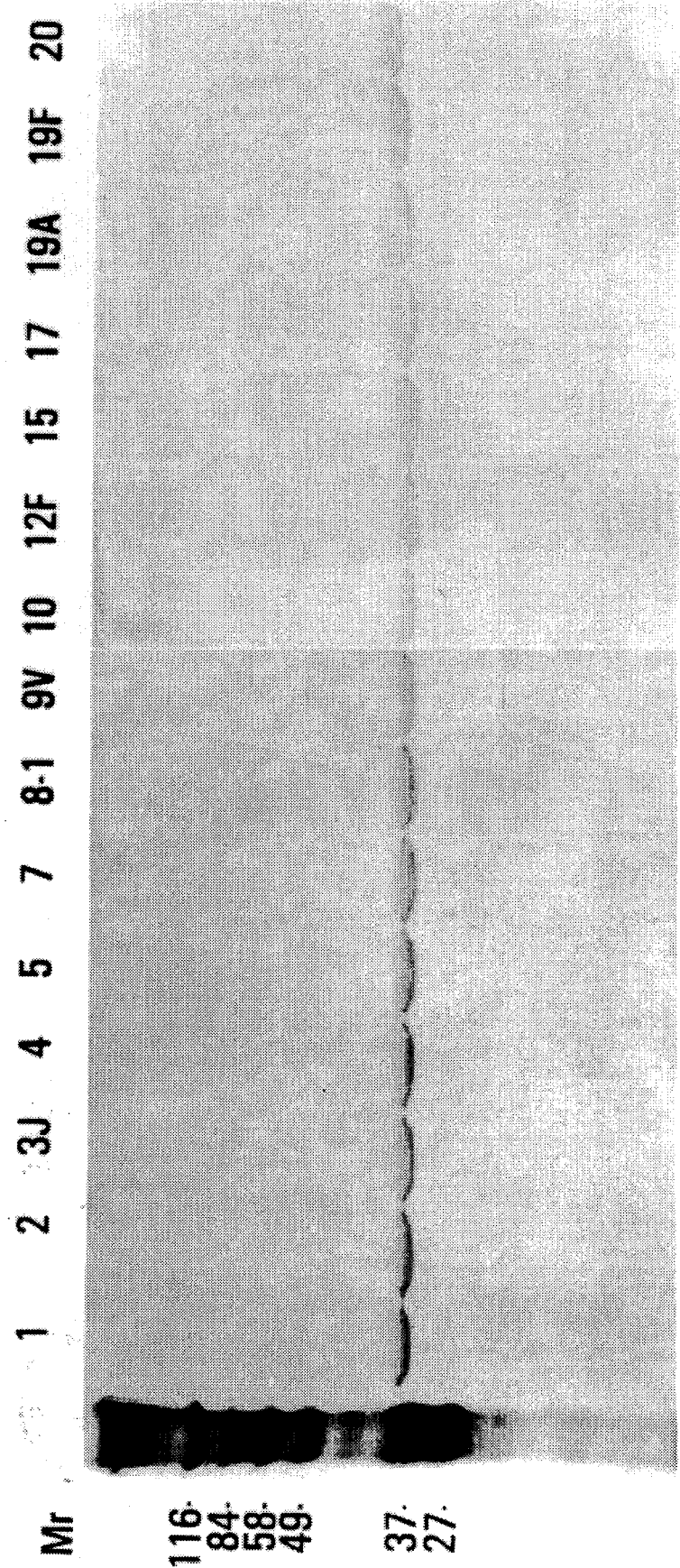
FIG. 6 shows the surveillance of the 43 kDa hemin/hemoglobin-binding protein among serotypes of Streptococcus pneumoniae.

Surveillance of 43-kDA hemin/hemoglobin-binding protein among serotypes of *Streptococcus pneumoniae*. To investigate whether hemin/hemoglobin-binding protein can be found in all serotypes of *Streptococcus pneumoniae* and whether this protein, like PspA, is polymorphic, 16 serotypes of *Streptococcus pneumoniae* were obtained from the Center for Biologics Evaluation and Research, Food and Drug Administration. The assay showed that the anti-hemin-binding protein antibodies reacted with a 43-kDa protein in all serotypes of *Streptococcus pneumoniae* as shown in FIG. 6. This indicates that the molecular size and antigenicity of 43-Kda hemin/hemoglobin-binding protein are highly conserved.

EXAMPLE 8

Effect of Growth Condition on Hemoglobin Binding Activity.

An aliquot (200 µl) of overnight culture of Rx1 was transferred to 10 ml Todd Hewitt Broth (THB) supplemented with 600 µM EDDA (low-iron medium), and to 10 ml THB supplemented with 10 mM ferric sulfate (high-iron medium) After grown for another 6 h at 37° C., cells of both cultures were harvested, washed twice with 50 mM Tris-100 mM NaCl at pH 8.0 (TN buffer), and suspended in 1 ml of TN buffer. The absorbance at 600 nm of both high-iron and low-iron cell suspension was measured. Same amount of each cells ($A_{600\ nm}$ =0.6) were mixed with 7µg of biotinylated hemoglobin with gentle inverting at room temperature for 30 min. Treated cells were washed with TN buffer three times, suspended in 1 ml TN buffer, and incubated with 10 µl of 1:1,000 dilution of streptavidin conjugated alkaline phosphatase at room temperature for 30 min, washed three times with TN buffer and alkaline phosphatase buffer. The cell associated alkaline phosphatase activity resulted from the interaction between biotin and streptavidin was measured at 600 nm in the Beckman spectrophotometer using 5-bromo-4-chloro-3-indolyl phosphate as substrate. Changes in absorbance reflect the presence of hemoglobin binding activity. The results are as follows:

|   | Alkaline phosphatase (U/A600) |
|---|---|
| 1. low iron cells | 17.0, 14.8 |
| 2. high iron cells | 0 |

The studies illustrated that the hemoglobin binding activity of *Streptococcus pneumoniae* increases when iron is removed from the growth medium.

EXAMPLE 9

Effect of Hemoglobin and Hemin in Blocking the Binding of Hemoglobin to Pneumoccoal Cells.

To examine the binding specificity of hemoglobin, an aliquot (100 µl) of Rx1 cell suspension ($A_{600-m}$ 0.3) grown under low-iron conditions were mixed with biotinylated hemoglobin (5 µg) in the absence and presence of hemoglobin or hemin (5 µg) respectively. After incubation at room temperature for 30 min, each sample was washed with TN buffer three times and then suspended in 1 ml TN buffer. The cells were then incubated with 10 µl of 1:1000 of AP-streptavidin at room temperature for 30 min, washed three times with alkaline phosphatase (AP) buffer and suspended in 1 ml of AP buffer. The alkaline phosphatase activity was measured as described in Example 8. The results are as follows:

| Treatment | Alkaline phosphatase activity (U/$A_{600\ nm}$) |
|---|---|
| cells + Bio-Hb | 12.8 |
| cells + Hb + Bio-Hb | 9.6 |
| cells + Hemin + Bio-Hb | 6.4 |

The results were as follows:

| Results: | Alkaline phosphatase activity (U/A600) |
|---|---|
| 1. cells | 12.8 |
| 2. cells + Hb | 9.6 |
| 3. cells + Hemin | 6.4 |
| 4. cells + PIX | 67.2 |

These results show the inhibitory effect on non-labeled hemoglobin and hemin on the binding of biotinylated hemoglobin to pneumococcal cells.

EXAMPLE 10

Location of Hemoglobin Binding Proteins

A pure culture of *Streptococcus pneumoniae*, RX1 was used to inoculate 100 ml of in Todd Hewitt Broth overnight. The culture was grown for 24 hrs. Following, the optical density of the culture sample was measured at $A_{600}$. The cells were then harvested and washed twice with 50 mM Tris-100 mM NaCl, pH 8.0, (TN buffer) and suspended in buffer to an optical density at $A_{600}$ to 10. Four ml of cell suspension was subsequently incubated with 400 µg of biotinylated hemoglobin, RT for 1 h, washed with buffer 5 times and finally suspended in 4 ml of buffer. The cell suspension was then mechanically lysed with a bead beater and the suspension was microfuged at full speed for 5 minutes. The supernatant fraction was removed from the centrifuge and placed in a 50.3Ti rotor and centrifuged at 40,000 rpm for 1 h. The supernatant was collected and used as cytosol fraction. The pellet from this sample was resuspended in 4 ml of buffer, spun again and suspended in 1 ml of buffer. This was used as a particular fraction. The location of bound hemoglobin was determined by dot blot assay.

A. Dot Blot Assay

Both cytosol and particulate fractions were serial diluted with TN buffer. Two microliters of each dilution was spotted on 3×5 cm nitrocellulose paper, air dried, and blotted with blotto (1.5% skim milk in TBS), overnight. The nitrocellulose paper was incubated with 10 ml of blotto containing 1:7,000 dilution of streptavidin conjugated alkaline phosphatase for 1 h.

The results revealed that a small portion of bound hemoglobin was found in the cytosol fraction and the majority in the particulate fraction of *Streptococcus pneumoniae*. The particulate fraction is a mixture of the insoluble portion of the cell wall and cell membrane. The soluble fraction is a mixture of the soluble fraction of the cell wall and cytoplasm.

B. SDS-PAGE

To identify proteins responsible for the binding of biotinylated hemoglobin, 20 µl SA-agarose was added to both the cytosol and particulate fractions, mixed and incubated at room temperature for 30 min, The samples were then spun, and washed three times with TN buffer and finally suspended in 40 µl of two-fold concentrated SDS-PAGE sample buffer without DDT. The samples were then boiled for 5 min and centrifuged in microtupe. The supernatants were collected, mixed with 1 µl of 100 mM DDT and analyzed by SDS-PAGE.

Figure 7:
FIG. 7 shows the localization of the hemin/hemoglobin-binding proteins using SDS-PAGE.

The results are shown in FIG. 7. A major hemoglobin binding protein with an approximate molecular weight of 43 kDa were identified in the soluble fraction and a hemoglobin binding protein with an approximate molecular weight of 55 kDa was identified in the particulate fraction of *Streptococcus pneumoniae*. Since the 43 kDa proteins could react with hemoglobin before cells were disrupted, these results suggest that 43 kDa hemoglobin binding protein is located in the soluble fraction of cell wall which agrees with the observation described in Example 6.

EXAMPLE 11

Identification of Hemoglobin Binding Proteins Using Electroblotting.

Rx-1 cells were grown and mechanically lysed with glass beads and spun in a microfuge. The resulting supernatant was used as cell lysate. Three microliters of SA-agarose were mixed with 150 B1 of cell lysate and inverted at room temperature for 20 min to remove proteins that possibly bind to streptavidin aganosa aganosa. The cell sample was spun for 2 min, the supernatant was analyzed by SDS-PAGE.

Figure 8A:
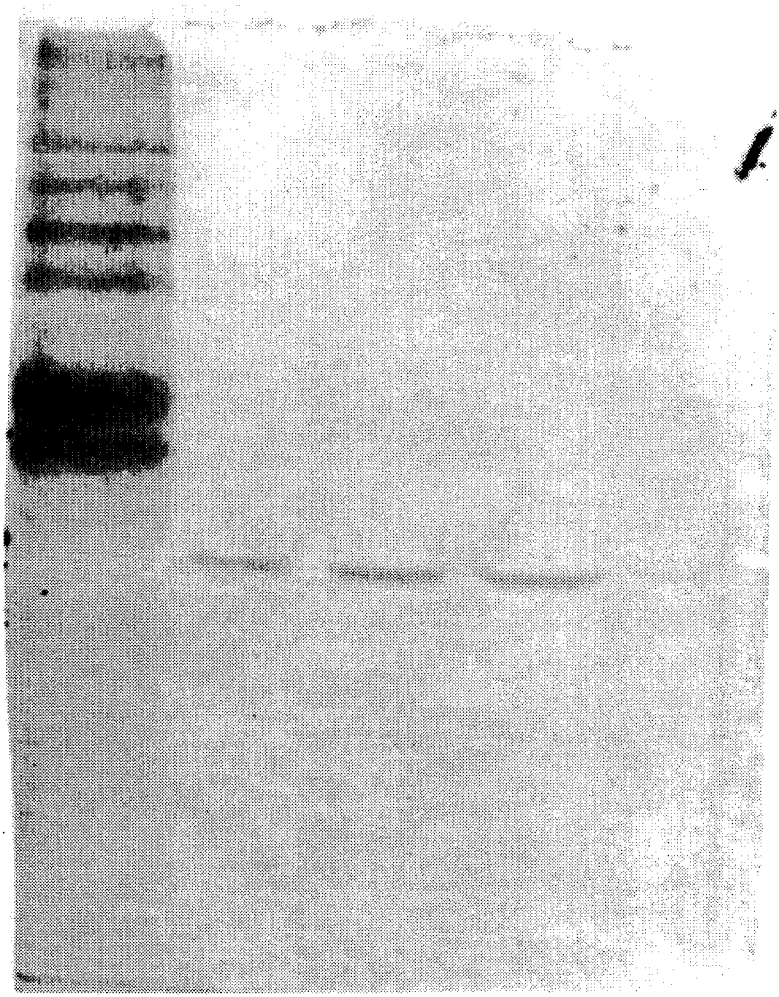
FIG. 8 shows the localization of the hemin/hemoglobin-binding proteins using electroblotting.
Figure 8B:
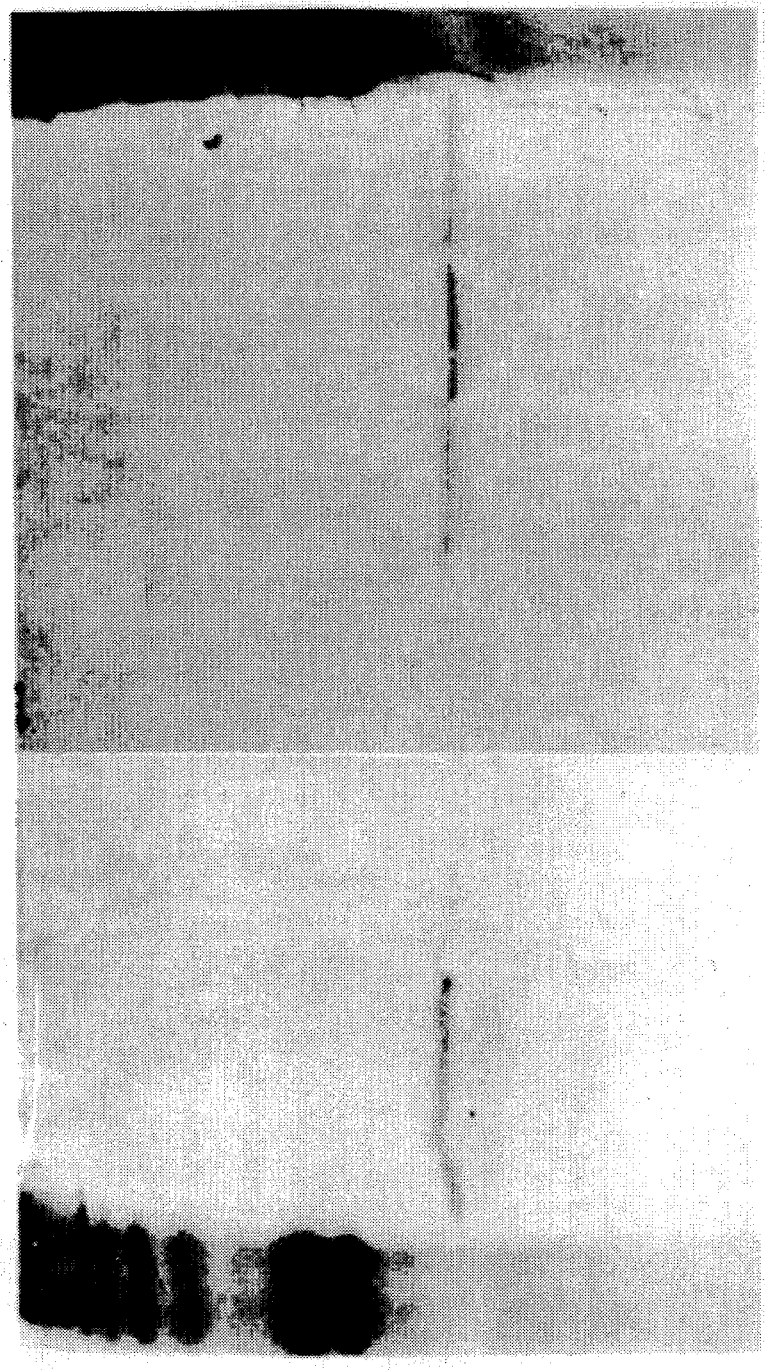

Electrophoretically separated proteins were transferred from gel to a piece of nitrocellulose paper, blotted with blotto for 1 h, and incubated with 10 ml of blotto containing biotinylated hemoglobin (500 mg/ml) at 37° C. for 2 h. Treated filter was then washed with blotto three times and incubated with 10 ml of blotto containing 1:7,000 dilution of AP-streptavidin, 1 h. Finally, the filter was washed with blotto twice and alkaline phosphatase buffer twice and the color developed. The results are shown in FIG. 8. These results identify a hemoglobin binding protein with an approximate molecular weight of 18 kDa which is localized in the cytoplasm of *Streptococcus pneumoniae*. This is the only hemoglobin binding protein that retained activity after SDS-PAGE.

We claim:

1. Antibodies which specifically bind an isolated hemin/hemoglobin-binding protein of *Streptococcus pneumoniae* having an approximate molecular weight of 43 kDa.

2. The antibodies according to claim 1 wherein said antibodies are monoclonal.

3. The antibodies according to claim 1 wherein said antibodies are polyclonal.

4. A method of detecting and diagnosing conditions caused by infectious *Streptococcus pneumoniae* comprising detecting the presence of a hemin/hemoglobin-binding protein of *Streptococcus pneumoniae* having an approximate molecular weight of 43 kDa and correlating the presence of hemin/hemoglobin-binding protein with a condition caused by infectious *Streptococcus pneumoniae*.

5. A method of detecting and diagnosing conditions caused by infectious *Streptococcus pneumoniae* comprising contacting a serum or spinal fluid sample with an antibody which specifically binds a 43 kDa hemin/hemoglobin-binding protein of *Streptococcus pneumoniae* and correlating the presence of antibody-antigen complexes with a condition caused by infectious *Streptococcus pneumoniae*.

6. A compartmentalized kit for detection of *Streptococcus pneumoniae* infections in humans comprising at least a first container adapted to contain an antibody having detectable specificity for a 43 kDa hemin/hemoglobin-binding protein of *Streptococcus pneumoniae*.

7. A method of detecting the presence of *Streptococcus pneumoniae* in a mammal comprising contacting a serum or spinal fluid sample with an antibody which specifically binds a 43 kDa hemin/hemoglobin-binding protein of *Streptococcus pneumoniae*, for a time and under conditions sufficient to form an antibody-antigen complex and correlating the level of the antibody-antigen complex with the presence or absence of *Streptococcus pneumoniae* in said mammal.

* * * * *

UNITED STATES PATENT AND TRADEMARK OFFICE
CERTIFICATE OF CORRECTION

PATENT NO.   : 5,474,905
DATED        : December 12, 1995
INVENTOR(S)  : Stanley Tai, et al.

It is certified that error appears in the above-indentified patent and that said Letters Patent is hereby corrected as shown below:

On the Title Page, Section [56], line 3: "436/252.1" should read --435/252.1--

Column 17, line 18: "($A_{600-m}$" should read --($A_{600-nm}$--

Column 18, line 40: "were" should read --was--

Column 18, line 57: "Bl" should read -- $\mu l$ --

Column 18, line 59: after "streptavidin" delete --aganosa aganosa--

Signed and Sealed this

Twenty-fifth Day of November, 1997

*Attest:*

*Attesting Officer*

BRUCE LEHMAN

*Commissioner of Patents and Trademarks*